US006515200B1

(12) United States Patent
Kobayashi

(10) Patent No.: US 6,515,200 B1
(45) Date of Patent: Feb. 4, 2003

(54) EUPHORBIA INTERSPECIFIC HYBRID PLANT

(75) Inventor: Ruth Kobayashi, Carlsbad, CA (US)

(73) Assignee: Paul Ecke Ranch, Inc., Encinitas, CA (US)

(*) Notice: Subject to any disclaimer, the term of this patent is extended or adjusted under 35 U.S.C. 154(b) by 0 days.

(21) Appl. No.: 09/690,370

(22) Filed: Oct. 16, 2000

(51) Int. Cl.$^7$ .............................. A01H 1/00; A01H 5/02; A01H 5/00; A01G 1/06; C12N 5/04

(52) U.S. Cl. .............................. 800/269; 47/6; 435/410; 435/430.1; 800/260; 800/295; 800/298; 800/323

(58) Field of Search .............................. 435/410, 430.1; 47/6; 800/269, 260, 295, 298, 323

(56) References Cited

U.S. PATENT DOCUMENTS 4,724,276 A   2/1988   Ecke, Jr. ........................ 800/1

OTHER PUBLICATIONS

Dehgan 1984, Phylogenetic significance of interspecific hybridization in Jatropha (Euphorbiacease). Systematic Botany 9(4):467–478.*

Dehgan, Phylogenetic significance of interspecific hybridization in Jatropha (Euphorbiaceae), *Sytematic Bot.*, 9(4):467–478, 1984.

Dole et al., "Investigations on the nature of a graft–transmissible agent in poinsetta", *Can. J. Bot.*, 71:1097–1101, 1993.

Dolezel et al., "Embryo development and in vitro culture of *Allium cepa* and its interspecific hybrids," *Z Pflanzenzucht*, 85:177–184, 1980.

Dressler, "A new and attractive poinsettia, Euphorbiaceae, from Guerrero, Mexico," *Bol. Soc. Bot. Mexico*, 35:17, 1975. Summary only.

Keller et al., "Interspecific crosses of onion with distant Allium species and characterization of the presumed hybrids by means of flow cytometry, karyotype analysis and genomic in situ hybridization," *Theor. Appl. Genet.*, 92:417–424, 1996.

Krauter et al., "Efficent interspecific hybridization in the genus Helianthus via 'embryo rescue' and characterization of the hybrids," *Theor. Appl. Genet.*, 82:521–525, 1991.

Le Duc and Albrecht, "Dogwood Poinsettia *Euphoriba cornastra* (Dressler) A. Radcliffe–Smith, A New Floral Pot Crop," *HorstScience*, 31:472, 1996.

Lee et al., "Phytoplasma induced free–branching in commercial poinsettia cultivars," *Nat Biotechnol*, 15(2):178–182, 1997.

Sorenson and Brewbaker, "Interspecific compatibility among 15 Leucaena species (Leguminosae: Mimosoideae) via artificial hybridizations," *Amer. J. Bot*, 81(2):240–247, 1994.

Suszwik, "The secret of free branching poinsettias," *Beltsville Area Research Highlights: 1998 Reprints from Agricultural Research*, p. 56, 1998.

* cited by examiner

Primary Examiner—David T. Fox
Assistant Examiner—David H Kruse
(74) Attorney, Agent, or Firm—Fulbright & Jaworski L.L.P.

(57) ABSTRACT

A new plant was created as an interspecific hybrid of the genus Euphorbia. The plant was created by the rescue of an embryo resulting from the cross-pollination of a cultivated Poinsettia, *Euphorbia pulcherrima*, with a seedling of the uncultivated *Euphorbia cornastra*. The new interspecific hybrid plant was found have unique traits that differed from either parent. The plant exhibited colorful flower bracts indicating desirable characteristics for ornamental use. In addition to providing the interspecific hybrid plant and parts thereof, the invention provides methods for making the same as well methods for creating interspecific hybrid plants having altered growth characteristics and the plants created thereby.

25 Claims, No Drawings

EUPHORBIA INTERSPECIFIC HYBRID PLANT

BACKGROUND OF THE INVENTION

1. Field of the Invention

The present invention relates generally to Euphorbia interspecific hybrid plants and methods for making the same. More particularly, it concerns interspecific hybrid plants derived from the cross of *Euphorbia pulcherrima* and *Euphorbia cornastra* and methods for the interspecific transfer of altered growth characteristics to this and other plants.

2. Description of Related Art

A characteristic of plants is the ability to cross with other species, called interspecific hybridization. Interspecific hybridization has been identified in a number of species. For example, within the genus Allium, a few crosses between onion (*A. cepa* L.) and its closest relatives of the section Cepa have proved successful (Van Raamsdonk et al. 1992). However, crosses of onion with species of other sections or subgenera were found mostly unsuccessful, including crosses with *A. angtilosuim* L., *A. schoenoprasum* L., *A. senescens* L. (Gonzalez and Ford-Lloyd 1987), and *A. sphaerocephalon* L. (Keller et al., 1996).

Interspecific hybridization has allowed creation of new forms of plants and the transfer desirable -features from one species into another, e.g., via introgression from wild into related cultivated species. However, the ability of any two species to create viable interspecific hybrid seeds or plants is unpredictable and often has proved impossible. In crosses where interspecific hybridization is possible in the greenhouse, in many cases no such hybridization will occur naturally. This may result from a number of factors, including, ethological factors such as pollinator specificity, e.g., where flowers differ morphologically, because of the need for human intervention to obtain viable embryos, or because of ecological separation.

A technique which has been used to increase the likelihood of obtaining viable interspecific hybrid plants is embryo rescue (Dolezel el al. 1980). However, even with embryo rescue, the ability to obtain interspecific hybrids is unpredictable and frequently has been completely unsuccessful, particularly in the case of distantly related species.

SUMMARY OF THE INVENTION

In one aspect, the invention provides an interspecific hybrid Euphorbia plant or part thereof derived from the cross of *Euphorbia pulcherrima* and *Euphorbia cornastra*. In one embodiment of the invention, the interspecific plant may be defined as comprising one or more characteristics selected from the group consisting of vibrant pink color, short day response for flowering, floriferous, free branching and attractive medium dark foliage. Further provided by the invention are any parts of the interspecific hybrid plant, including a flower, cutting, pollen, ovule or any other plant part, including a single cell or collection of cells of such a plant. Still further provided by the invention is an interspecific hybrid Euphorbia plant or part thereof clonally propagated from such a plant. By the term "clonally propagated," it is meant any generation of a Euphorbia interspecific hybrid plant clonally derived from a plant provided by the instant invention. Such clonal propagation may be carried out, for example, by taking a cutting of a plant and cultivating the cutting such that it produces roots. The rooted cutting may then be grown as a new plant which is a clone of the starting plant. Clonal propagation may be carried out an essentially unlimited number of times to produce great numbers of clonally propagated plants, each of which is essentially identical to the starting plant from which the cutting is taken.

In another aspect, the invention provides a process of producing an interspecific hybrid Euphorbia plant or part thereof In one embodiment of the invention, the process comprises crossing a *Euphorbia pulcherrima* plant to a *Euphorbia cornastra* plant. The process may still further be defined as comprising the steps of (a) cultivating first and second plants, wherein either the first plant is a *Euphorbia pulcherrima* plant and the second plant is a *Euphorbia cornastra* plant, or the first plant is a *Euphorbia cornastra* plant and the second plant is a *Euphorbia pulcherrima* plant; (b) collecting pollen from the first plant, (c) pollinating a flower on the second plant with the pollen; and (d) obtaining an interspecific hybrid plant resulting from the pollinating. The process may still further be defined as comprising embryo rescue of an embryo resulting from the pollinating. In particular embodiments of the invention, the first plant is a *Euphorbia pulcherrima* plant and the second plant is a *Euphorbia cornastra* plant, while in other embodiments the first plant is a *Euphorbia cornastra* plant and the second plant is a *Euphorbia pulcherrima* plant. In yet another aspect, the invention provides a plant or any part thereof produced by crossing a *Euphorbia pulcherrima* plant to a *Euphorbia cornastra* plant, including any clonal propagations thereof.

In still yet another aspect, the invention provides a process of preparing an interspecific hybrid Euphorbia plant or part thereof comprising the steps of: a) obtaining a cutting of an interspecific hybrid Euphorbia plant derived from the cross of *Euphorbia pulcherrima* and *Euphorbia cornastra*; and b) cultivating said cutting to obtain an interspecific hybrid Euphorbia plant. Accordingly, any derivatives of a plant derived from the cross of *Euphorbia pulcherrima* and *Euphorbia cornastra* are specifically within the scope of the invention. As such, those of skill in the art will recognize that once a Euphorbia interspecific hybrid plant is prepared, it may be propagated for a potentially unlimited number of generations. Each plant produced by such a method and the process for the propagation additionally form a part of the instant invention. One such process of propagating may comprise applying a hormone composition to a cutting of a plant of the invention to induce formation of roots, although any other process of propagating a plant of the invention could potentially be used.

In still yet another aspect, the invention provides a process of altering the plant growth characteristics of an interspecific hybrid Euphorbia plant derived from the cross of *Euphorbia pulcherrima* and *Euphorbia cornastra*, or a part thereof, the process comprising the steps of (a) providing a plant having free-branching characteristics to be used as understock, (b) providing a scion of an interspecific hybrid. Euphorbia plant derived from the cross of *Euphorbia pulcherrima* and *Euphorbia cornastra*; (c) making a graft union between the cellular tissue of the understock plant and scion plant, whereby the characteristics of a vegetative shoot arising from said scion of said interspecific hybrid Euphorbia plant are altered; and (d) cultivating said shoot to obtain an interspecific hybrid Euphorbia plant comprising altered growth characteristics. Exemplary growth characteristics that may be altered by the technique are branching characteristics, such as exhibition of the free-branching phenotype.

In still yet another aspect, the invention provides an interspecific hybrid Euphorbia plant or part thereof which has been prepared by a method comprising the steps of: (a) providing a plant having free-branching characteristics to be used as understock; (b) providing a scion of an interspecific hybrid Euphorbia plant derived from the cross of *Euphorbia pulcherrima* and *Euphorbia cornastra*; (c) making a graft union between the cellular tissue of the understock plant and scion plant, whereby the characteristics of a vegetative shoot arising from the scion of the interspecific hybrid Euphorbia plant are altered; and (d) cultivating the shoot to obtain an interspecific hybrid Euphorbia plant comprising altered growth characteristics, Included within the invention are any parts of such a plant, including a flower, cutting, pollen, an ovule, or cell or any other part of the plant. Still further provided by the invention is an interspecific hybrid Euphorbia plant or part thereof clonally propagated from such a plant.

In still yet another aspect, the invention provides a process of altering the plant growth characteristics of a target plant by use interspecific grafts. In one embodiment of the invention, the process comprises the steps of: (a) providing a plant having free-branching characteristics to be used as understock; (b) obtaining a scion of a target plant, wherein said plant having free-branching characteristics and said target plant are of different species; (c) making a graft union between the cellular tissue of the understock plant and the scion, whereby the characteristics of a vegetative shoot arising from said scion are altered, and (d) cultivating said shoot to obtain a target plant comprising altered growth characteristics. In another embodiment of the invention, the target plant is further defined as from the genus Euphorbia, and may still further be defined as a species selected from the group consisting of *Euphorbia cornastra, Euphorbia heterophylla, Euphorbia cyathophora, Euphorbia fulgens, Euphorbia leucocephala* and *Euphorbia marginata*. In particular embodiments of the invention, the target plant may be any non-succulent species of the genus Euphorbia. The understock plant may be of any desired species capable of transmitting the trait, including *Euphorbia pulcherrima*. Exemplary understock plants include, but are not limited to, the *E. pulcherrima* varieties Annette Hegg Dark Red, V-14 Glory, Peterstar and Freedom. Alternatively, the understock plant may further be defined as a *Euphorbia fulgens, Euphorbia cornastra* or other suitable Euphorbia species.

In still yet another aspect, the invention provides a plant produced by an interspecific graft, for example, as described above. In one embodiment of the invention, the plant may be produced by a method comprising the steps of: (a) providing a plant having free-branching characteristics to be used as understock, (b) obtaining a scion of a target plant, wherein said plant having free-branching characteristics and said target plant are from different species, (c) making a graft union between the cellular tissue of the understock plant and the scion, whereby the characteristics of a vegetative shoot arising from said scion are altered, and (d) cultivating said shoot to obtain a target plant comprising altered growth characteristics. Also provided by the invention is a part of such a plant, including a flower, cutting, pollen, an ovule or a cell.

DETAILED DESCRIPTION OF THE INVENTION

The invention provides a new plant with unique characteristics and attractive flower bracts, desirable for an ornamental plant. The new plant is an interspecific hybrid, not previously known, created in Encinitas, Calif. The plant was the result of the surprising finding that an interspecific hybrid may be produced from the cross of *Euphorbia pulcherrima* and the uncultivated species *Euphorbia cornastra*. The inventor found that failure of the hybrid zygote to naturally develop in the seedpod could be overcome by excision of newly formed embryos from the seedpod, followed by growth to a plantlet on nutrient agar medium. Cultured plantlets could then be transplanted to a greenhouse-growing medium where they developed into mature interspecific plants.

The invention also provides methods for creating plants with novel characteristics. In particular, one embodiment of the invention relates to the surprising discovery that the free-branching trait and associated phenotypic characteristics can be transferred byway of interspecific grafts. Significantly, the free-branching trait was found to have been permanently introduced into the interspecific hybrid plant described herein through interspecific grafting to *E. pulcherrima* understock (see Example 2 and Table 1). The grafting technique avoided the need to use a parasitic dodder for interspecific transfer of the phytoplasma associated with the free-branching trait (see, e.g., Lee et al., 1997).

Description of the Plant

The interspecific hybrid plant provided by the invention exhibits unique characteristics unlike either of the parent species. For example, *Euphorbia pulcherrima* is a "short day" plant with respect to flower initiation, while *Euphorbia cornastra* is a "long day" plant. However, the interspecific hybrid flowered in response to short days and the time to full flower development was found to be a relatively short 6 weeks compared to the *E. pulcherrima* parent that took 9 weeks for flower development under the same growing environment.

Table 1 provides a detailed description of the new *E. pulcherrima×E. cornastra* interspecific hybrid plant as observed in Encinitas, Calif, USA during May 18, 2000. Observations were recorded from flowering plants, grown as one branched plant per pot. The pot was 17 cm in diameter and 13 cm in height. Color designations are based on comparison to the 1986 edition of RHS Colour Chart, first published in 1966 by the Royal Horticultural Society, London, England. The *E. pulcherrima×E. cornastra* plant described in Table 1 was converted to the free-branching phenotype in accordance with Example 2, thereby enhancing the characteristics of the plant for use as an ornamental. The ungrafted (e.g., unbranched) *E. pulcherrima×E. cornastra* interspecific hybrid plant was similar in appearance to the free-branching plant, with the exception that after pinching the top 2–4 lateral branches developed, as opposed to all lateral buds developing fairly evenly. The resulting plant was slightly taller and individual blooms (bracts+cyathia) were slightly bigger (10–25%). The foliage color and shape were substantially the same, but the foliage shape appeared to vary somewhat in that some leaves had indented leaf margins and some had entire leaf margins. Such variation in leaf morphology is common in *E. pulcherrima*. It will be understood to those of skill in the art that the description in Table 1 is included herewith for illustrative purposes only and is not limiting. In particular, it will be understood that traits and measurements may vary, for example, due to environmental conditions or other variables. Accordingly, any plant or part thereof derived from the cross of *E. pulcherrima* and *E. cornastra* is within the scope of the instant invention.

TABLE 1

Detailed description of free-branching *E. pulcherrima* x *E. cornastra* interspecific hybrid plant as observed in Encinitas, CA, USA during May 2000.

| | |
|---|---|
| Origin: | An interspecific hybrid created by cross-pollinating a cultivated *Euphorbia pulcherrima* plant with an uncultivated *Euphorbia cornastra* plant. |
| Classification: | Botanical-Euphorbia X hybrid |
| Form: | Shrub |
| Height: | Short–medium |
| Growth Habit: | Flowering was observed, branched plant in a pot with an overall height of 42 cm, including the pot and an overall width of 42 cm. The plant grew upright but was somewhat spreading. The average bract diameter of individual flowers was 20 cm. |
| Branching: | Lateral branches develop and terminate in a flower without pinching. However, when pinched before flower induction to remove terminal dominance, all lateral branches develop uniformly and at a faster rate. The plant of description was pinched leaving 12 nodes on the stem. Strong lateral branches of nearly equal length and vigor arose, one from each stem node, resulting in a plant with 12 lateral branches. The lowermost lateral had 14 nodes and the uppermost, 9 nodes subtending the flower. |
| Growth Rate: | Rooting of stem cutting occurs in 18–21 days under intermittent mist. The plant will flower in about 6 weeks under continuous long night conditions and night temperatures of about 16–18 degrees C. |
| Foliage: | The foliage is clean and dark green from bottom to top of the plant. The leaves are of medium size, leaf blades typically 10 cm long and 5 cm wide for the larger lower leaves and 6 cm long and 2.5 cm wide for the smaller upper leaves. Leaf petioles are green and 6 cm long on the larger leaves to 3 cm on the smaller leaves. The upper leaf surface is glabrous, but slightly rugose and the under surface is finely pubescent. |
| Leaf shape: | Leaves are elliptic with acute bases and acuminate tips. Leaf margins are entire. |
| Color: | Upper side—Dark green, darker than RHS 139A Under—Green, near RHS 147B |
| Bracts: | There were 2–4 pink transitional bracts at the upper stem nodes just below the inflorescence. These were 7–8 cm long and 3 cm wide. Eight to 10 bracts subtending the cyathia varied in size from 5 cm long and 2 cm wide to 1.5 cm long and 1 cm wide. |
| Shape: | Bracts are elliptic with acute bases and acuminate tips. Bract margins are entire. |
| Color: | Upper side—Pink, near RHS 57D Under side—Grayish-White, near RHS 156D |
| Flowers: | Generally, 8–10 rudimentary and sterile cyathia (flowers) were present at maturity. Each cyathium was about 5 mm long and 3 mm wide and green in color. |

II. Interspecific Grafts for Introduction of Altered Growth Characteristics

The current invention demonstrates, for the first time, that interspecies grafts may be used for the introduction of altered growth characteristics into a plant species. In particular, it is demonstrated herein that grafting may be used to transfer the free-branching trait, as well as associated traits, to species other than that of the understock plant. Such an alteration was demonstrated through use of an *E. pulcherrima* understock and a *E. pulcherrima*×*E. cornastra*, hybrid scion, as described in Example 2. A phenotypic description of the resulting plant is given in Table 1.

While within-species grafting to transfer the free-branchingtrait has been described in *Euphorbia pulcherrima* (see, for example, U.S. Pat. No. 4,724,276, the disclosure of which is specifically incorporated herein by reference in its entirety), the lack of techniques describing interspecific grafting for transfer of free-branching has limited the applicability of the technique.

The free-branching trait found in Poinsettia cultivars can be contrasted with plants which are restricted in their branching habit. The main difference is the propensity of shoots to elongate at the lower nodes. Restricted branching cultivars exhibit strong apical dominance as only a few (1 to 3) axillary shoots grow after the terminal growing point has been removed (pinched). Free-branching cultivars form many axillary shoots depending on the number of nodes that remain after pinching. Consequently, restricted branching cultivars produce fewer vegetative cuttings and when such plants are placed under short days, restricted branching cultivars produce fewer inflorescences.

Branching traits can be altered by grafting plant scions onto understock of plants which are free-branching. Specifically, the free-branching characteristic may be imparted to target plant species, including the Euphorbia interspecific hybrid plant described herein, as follows. First, the process is carried out under a photoperiod designed to prevent "flowering." Scions of the plant to be altered are then grafted onto understock of the plant which is free-branching. The new growth of the scion has a vegetative shoot or stem which is, over time, altered. Grafting can be accomplished by any of the several well known established and commonly known grafting techniques or methods. After the graft union has become established, or healed by cell division, the free-branching characteristic is transferred from the understock into the scion and this newly grafted plant is allowed to grow in a normal manner under long day conditions. Cuttings taken from the scion portion of the grafted plant are free-branching, whereas the scion possessed restricted branching characteristics before grafting. The change is stable and uniform and appears to be firmly fixed.

The techniques for interspecific transfer of the free-branching trait were used to alter the phenotype of the *E. pulcherrima*×*E. cornastra* interspecific hybrid plant provided by the invention, as is described in Example 2. As can be seen in Table 1, the introduction of the free-branching trait into the interspecific hybrid plant resulted in an altered branching phenotype, generally improving the characteristics of the plant for use as an ornamental.

Free-branching is one of the most obvious plant characteristics which results from the grafting process. Other plant characteristics may also be modified or altered by the grafting process, including leaf morphology, such as the amount of lobing; flowering response such that the new cultivar flowers earlier or later than the original scion cultivar; leaf color modifications, such that the green leaves and colored bracts are lighter or darker, stem diameter; internode length number of cuttings; dates of flowering; and the capacity of the plant to form abscission layers at the base of leaves and bracts under stress.

Use of interspecific grafting is specifically envisioned in conjunction with any Euphorbia species, for example, *Euphorbia pulcherrima, Euphorbia cornastra, Euphorbia heterophylla, Euphorbia cyathophora, Euphorbia fulgens, Euphorbia leucocephala* and *Euphorbia marginata*. In particular embodiments of the invention, species use for interspecific grafting are any non-succulent species of the genus Euphorbia. Preferred understock for grafting include, for example, the *Euphorbia pulcherrima* varieties Freedom ("490"; U.S. Plant Pat. No. 7,825, the disclosure of which is incorporated herein by reference in it's entirety), Success Red ("559"; U.S. Plant Pat. No. 8,773, the disclosure of which is incorporated herein by reference in it's entirety), Red Velvet ("841"; U.S. Plant Pat. No. 11,124, the disclosure of which is incorporated herein by reference in it's entirety), Peterstar (U.S. Plant Pat. No. 8,259 the disclosure of which is incorporated herein by reference in it's entirety), Annette Hegg Dark Red (U.S. Plant Pat. No. 3,160, the disclosure of which is incorporated herein by reference in it's entirety), and V-14 Glory (U.S. Plant Pat. No. 4, 384, the disclosure of which is incorporated herein by reference in it's entirety), as well as the *Euphorbia fulgens* varieties Ahrku White, Ahrku Yellow and Ahrku Orange, although other such understock may be used and will be known to those of skill in the art.

III. Parent Plants and the Production of the Interspecific Hybrid Plant of the Invention The invention provides, for the first time, interspecific hybrid plants and parts thereof derived from the cross of *Euphorbia pulcherrima* and *Euphorbia cornastra*. In particular, the inventor has shown that interspecific crosses may be made between cultivated varieties of *Euphorbia pulcherrima* and the wild species *Euphorbia cornastra* to obtain plants having desirable ornamental characteristics. As such, the invention encompasses interspecific hybrid plants produced by the cross of any *Euphorbia pulcherrima* plant with a *Euphorbia cornastra* plant. In such hybrid crosses, there is a ("male") pollen donor plant, as well as the "female" pollen recipient plant, although it will be recognized that each plant possesses male and female flowers. In accordance with the invention, the plant used as the male or female in the cross may from either *Euphorbia pulcherrima* or *Euphorbia cornastra*. The choice of which plant to use as the male or female will generally depend upon viable pollen availability and/or the receptivity of female flower parts to pollination at the time the cross is made.

In a preferred embodiment, crossing comprises the steps of:

(a) cultivating first and second plants, wherein either the first plant is a *Euphorbia pulcherrima* plant and the second plant is a *Euphorbia cornastra* plant, or the first plant is a *Euphorbia cornastra* plant and the second plant is a *Euphorbia pulcherrima* plant;
(b) collecting pollen from the first plant;
(c) pollinating a flower on the second plant with the pollen; and
(d) obtaining an interspecific hybrid plant resulting from the pollinating.

The *Euphorbia pulcherrima* and *Euphorbia cornastra* plants crossed in accordance with the invention may, in one embodiment of the invention, be selected for one or more desired traits prior to the crossing. Such selection may comprise one or more cycles of crossing of the progenitors of the parent plant followed by selection for the desired trait(s). For example, one of skill in the art could, in view of the instant disclosure, select an *E. pulcherrima* and/or an *E. cornastra* parent plant having desired flower characteristics, including flower size or color, and expect those characteristics to influence the flower characteristics of an interspecific plant derived therefrom. In this way, one could potentially enhance the characteristics of the interspecific hybrid plant of the invention for use as an ornamental.

In crosses carried out in accordance with the invention, it may be desirable to use embryo rescue following pollinating to obtain viable interspecific hybrid plants, as described herein above, as mature seeds resulting from the interspecific hybrid crosses have generally been found by the inventor to have low rates of viability. It may also be desired to manipulate the photoperiod and/or other growth conditions of the parent plants in order to ensure synchronization of viable pollen and pollen-receptive flowers on the respective parent plants. Advantageously, during this stage, plants may be treated with fertilizer and/or other agricultural chemicals as considered appropriate.

At the time of flowering, the flower to be pollinated on the plant used as a female may be emasculated to avoid self-pollination, although this may be unnecessary where the parent plant exhibits a high degree of self incompatibility, as may be common among *E. pulcherrima* varieties. Emasculation can be achieved manually or could potentially be carried out using a chemical gametocide to sterilize the pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety.

The parent plants from which the interspecific hybrid plant of the invention was obtained, *Euphorbia pulcherrima* and *Euphorbia cornastra*, are both known and available to the public. The parent plant *Euphorbia pulcherrima*, commonly known as the Poinsettia or Christmas Poinsettia is widely cultivated and is publicly available by way of numerous cultivated varieties. These varieties may be clonally propagated by cuttings, as is well known to those of skill in the art (Ecke et al., 1990, the disclosure of which is specifically incorporated herein by reference in it's entirety).

The second parent plant, *Euphorbia cornastra*, is commonly known as the Dogwood Poinsettia and is a fairly recently discovered Euphorbia from Guerrero, Mexico (lat. 17°35'N, long. 99°54'W) (Le Duc and Albrecht, 1996). The species was collected in 1973 and described as a new species by Dressier (1975). The native habitat of the species is tropical deciduous forests at high elevations (1930m), where it can be found growing in rich humus soil at the foot of large limestone outcrops.

As described by Le Duc and Albrecht (1996), *E. cornastra* has pure-white bracts and summer flowering and is similar to the *E. pulcherrima* with regard to growth habit and inflorescence, but differs in foliage characteristics. For example, *Euphorbia cornastra* has pure-white bracts and gray-green foliage. The species has hollow stems that arise from a woody basal trunk and may attain a height of 2 meters or more. The true leaves of *E. cornastra* are attached by reddish petioles and are dark gray-green with a white pubescence that is most pronounced on the abaxial surface. The terminal floral display of pure-white bracts surrounding a compound cyme can reach 13 cm in diameter. In Manhattan, Kans., once daylength conditions were <10 hours, plants entered dormancy. Visible signs of growth were present when the daylength was >11 hour. Plants produced flowers at terminals of all shoots within 2 months of shoot growth initiation. Actively growing plants flowered every 2 to 3 months. Flowers were produced within 16 weeks of initiation of a greenhouse production period and had an effective postharvest life of at least 1 week for pot plants. Propagation of tip cuttings as well as from seed is possible (Le Duc and Albrecht, 1996).

IV. Identification of interspecific Hybrid Plants

Once an interspecific cross is made, it is important to identify resulting progeny as hybrid and not simply the result of selfing or pollination with pollen from another plant of the same species. One method for identification is morphological evaluation, provided that the interspecific hybrid has sufficient distinguishing characteristics, as is the case here. In particular, the characteristics described herein allow one of skill in the art to identify a plant as a *E. pulcherrima*× *E. cornastra* interspecific hybrid plant based on the physical characteristics of the plant. However, other techniques may also find use with the invention and may avoid potential errors caused by environmental variation. For example, if the parents differ in genome size, flow cytometric or other measurement of DNA content may detect hybrids at early developmental stages. However, since differences in DNA content may be due to reasons other than hybrid status, additional methods of analysis may be desired. As soon as root tips are developed, karyotype analysis can be performed, provided that the parental complements differ in size, number and/or morphology. Other alternatives include use of genomic in situ hybridization (GISH) (Schwarzacher et al. 1989) or genetic marker analysis.

Genetic markers represent an efficient method for analysis and identification of interspecific hybrid plants, and in particular, the combination of genetic complements from *Euphorbia pulcherrima* and *Euphorbia cornastra* parental plants. As used herein, the phrase "genetic complement" means an aggregate of nucleotide sequences which defines the identity of a plant or a cell of that plant. By way of example, the Euphorbia interspecific hybrid provided herein could be genotyped to determine a representative sample of the inherited markers it possesses relative to exemplary *Euphorbia pulcherrima* and *Euphorbia cornastra* parent plants. Genetic markers are alleles at a single locus. They are preferably inherited in codominant fashion so that the presence of both alleles at a diploid locus is readily detectable, and they are free of environmental variation, i.e., their heritability is 1. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. A preferred type of genetic marker is simple sequence repeats (SSRs), in that they are generally highly polymorphic and inexpensive to score. However, potentially any other type of genetic marker could be used, for example, restriction fragment length polymorphisms (RFLPs), amplified fragment length polymorphisms (AFLPs), single nucleotide polymorphisms (SNPs), and isozymes, to identify a plant of the invention.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Creation of *Euphorbia pulcherrima×Euphorbia cornastra* Interspecific Hybrid Plants In December 1997 a plant of *Euphorbia pulcherrima* known as 'M-6', a Paul Ecke Ranch proprietary variety, was crossed with the pollen from a plant of *Euphorbia cornastra*. The crossing was carried out by transfer of mature pollen of *E. cornastra* onto a receptive stigmatic surface of an *E. pulcherrima* flower with a fine paintbrush. Stigma receptivity was determined visually. Stigmas were considered receptive when they started to reflex open. The stigmas remained receptive for approximately 36 hours thereafter. Due to low self compatibility, emasculation of cyathia was not necessary to achieve interspecific hybridization between *E. cornastra* and *E. pulcherrima*.

Approximately 3 weeks after pollination, capsules that showed visible signs of swelling were collected and surface sterilized by immersion in 30% (v/v) commercial bleach solution (Chlorox 5.25%, sodium hypochlorite) for 25 minutes and rinsed with sterile water.

Embryos at the globular shaped stage of development, including suspensor cells, were excised and cultured on media containing Murashige and Skoog salts and vitamins, 6% sucrose, 0.15% activated charcoal and 0.75% Phytagar. Cultures were maintained at 26–27° C. day and 18–19° C. night temperature under 16 hour photoperiod provided by a mixture of cool-white and Grow-lux fluorescent light. After approximately 3 to 4 weeks, a mass (less than 1 mm in diameter) of yellow green friable callus and somatic embryos developed from the zygotic embryo tissue.

Developing callus and somatic embryos were subcultured onto fresh media every 4 to 6 weeks. After 4 months in culture, plantlets developed from the somatic embryos. Plantlets were transferred to the same media, but with only 3% sucrose. Plantlets continued to grow and after one month were transplanted to greenhouse growing medium of 70% Canadian peat moss and 30% perlite.

Subsequent to the original cross, interspecific crosses between various cultivars of *E. pulcherrima* and *E. cornastra* were found to yield embryos that, when cultured in the manner described above, developed into plantlets of hybrid origin. Rates of fertilization varied among 9 cultivars of *E. pulcherrima* crossed with *E. cornastra*, with individual rates using *E. pulcherrima* as the female parent, based on embryos that developed in culture, ranging from 0% to 30%. Reciprocal crosses between *E. pulcherrima* and *E. cornastra* were not attempted. The flowers of the hybrid appeared to have low pollen fertility. Aceto-carmine pollen staining indicated approximately 18% pollen viability, although percent pollen viability (stainability) can vary among *E pulcherrima×E. cornastra* hybrids, e.g. a full-sib of the plant described above had 3% pollen stainability. A well developed gynoecium was not observed.

Example 2

Preparation of Free-Branching Euphorbia Interspecific Hybrid Plants

Interspecific hybrid plants created by crossing *E. pulcherrima* and *E. cornastra*, as described in Example 1, were found to exhibit strong terminal dominance with little lateral branch development. To induce lateral branching, the new plant was grafted onto a "self-branching" understock of *E. pulcherrima* variety V-14 Glory (U.S. Plant Pat. No. 4384) through application of the procedures set forth in U.S. Pat. No. 4,724,276, the disclosure of which is specifically incorporated herein by reference in its entirety. In particular, rooted or unrooted cuttings of *Euphorbia pulcherrima* variety V-14 Glory and the interspecific hybrid were grafted together by an approach graft technique. A small piece of stem was removed along a smooth section of the cutting below the terminal shoot, approximately 1 inch long, cut about a quarter of the way through the skin, exposing the cambium of the understock V-14 Glory. A similar piece of stem was removed from the scion from the interspecific hybrid, and the cambiums of the two cut surfaces were matched together and bound together by wrapping with plastic tape. The grafted cuttings were propagated in sand under mist for root initiation and transplanted into peatmoss and perlite growing media.

After approximately 1–2 weeks under mist propagation, a callus union was observed along with root initiation of both cuttings. After 4 weeks, the terminal shoot of the V-14 Glory understock plant was removed above the graft union. The interspecific hybrid scion shoot was left to grow for 2 additional weeks, at which time the shoot tip was pinched (removed) about 5–7 nodes above the graft union. Lateral shoots developed above the graft union. New roots formed in 3 weeks. Plants were placed under a black plastic covering for 14 hours each night to induce flowering, beginning on Apr. 11, 2000. By May 18 flower bracts were fully developed. The results of a phenotypic analysis of the plant are given above, in Table 1, and demonstrate the transmission of the free-branching trait. The phenotypic traits described were found to persist in the altered plant, without loss of the free-branching trait. The results of the procedure yielded the surprising finding that interspecies grafts may be used to transmit the free-branching characteristic.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Alice Le Duc and Mary Lewnes Albrecht (1996) "Dogwood Poinsettia [*Eliphorbia cornastra* (Dressler) A. Radcliffe-Smith], A New Floral Pot Crop," HortScience 3193): 472.

Bijan Dehgan (1984) "Phylogenetic Significance of Interspecific Hybridization in Jatropha (Euphorbia)," Symtematic Botany, 9(4): pp. 467–478.

Dolezel J, Novak FH, Luzny J (1980) Embryo development and in vitro culture of *Allium cepa* and its interspecific hybrids. Z Pflanzenzucht 85:177–184.

Dressler, R L. (1975) "A new and attractive poinsettia, Euphorbia, from Guerrero, Mexico," Bol. Soc. Bot. Mexico 35:17.

Ecke, Paul Jr., Matkin, O. A., and Hartley, David E., "The Poinsettia Manual," Published by Paul Ecke Poinsettias, Encinitas, Calif., (1990)

Gonzalez L G, Ford-Lloyd B V (1987) "Facilitation of wide-crossing through embryo rescue and pollen storage in interspecific hybridization of cultivated Allium species," Plant Breed 98:318–322.

Keller, E. R. J., Schubert, i., Fuchs, J., and Meister, A., (1996) "Interspecific crosses of onion with distant allizim species and characterization of the presumed hybrids by means of flow cytometry, karyotype analysis and genomic in situ hybridization," Theor Appl. Genet., 92: 417–424.

Lee I M, Klopmeyer M, Bartoszyk I M, Gundersen-Rindal D E, Chou T S, Thomson K L, Eisenreich R (1997) "Phytoplasma induced free-branching in commercial poinsettia cultivars," Nat Biotechnol Feb;15(2):178–82.

Nomura Y, Maeda M. Tsuchiya T, Makara K (1994) "Efficient production of interspecific hybrids between *Allium chinense* and edible Allium spp. through ovary culture and pollen storage," Breed Sci 44:151–155.

Schwarzacher T, Leitch A R, Bennett M D, Heslop-Harrison J S (1989) "In situ localization of parental genomes in a wide hybrid," Ann Bot 64,315–324

Van Raamsdonk L W D, Wietsma W A, de Vries J N (1992) "Crossing experiments in *Allium L*. section Cepa." Bot J Linn Soc 109:293–303

What is claimed is:

1. An interspecific hybrid Euphorbia plant produced from a cross between *Euphorbia pulcherrima* as a female parent and *Euphorbia cornastra* as a male parent.

2. The interspecific hybrid Euphorbia plant of claim 1, further defined as comprising a phytoplasma, wherein said phytoplasma confers free-branching to said interspecific hybrid Euphorbia plant.

3. A plant part of an interspecific hybrid Euphorbia plant produced from a cross between *Euphorbia pulcherrima* as a female parent and *Euphorbia cornastra* as a male parent.

4. The plant part of claim 3, further defined as a flower.

5. The plant part of claim 3, further defined as a cutting.

6. The plant part of claim 3, further defined as pollen.

7. The plant part of claim 3, further defined as an ovule.

8. The plant part of claim 3, further defined as a cell.

9. An interspecific hybrid Euphorbia plant or part thereof clonally propagated from the plant of claim 1.

10. A process of producing an interspecific hybrid Euphorbia plant comprising crossing a *Euphorbia pulcherrima* plant with a *Euphorbia cornastra* plant, rescuing an embryo resulting from the crossing and obtaining an interspecific hybrid Euphorbia plant grown therefrom, wherein the *Euphorbia cornastra* plant is used as a male parent and wherein the *Euphorbia pulcherrima* plant is used as a female parent.

11. The process of claim 10, further defined as comprising the steps of:

(a) cultivating first and second plants, wherein the first plant is a *Euphorbia cornastra* plant and the second plant is a *Euphorbia pulcherrima* plant;

(b) collecting pollen from the first plant;

(c) pollinating a flower on the second plant with said pollen;

(d) isolating an embryo resulting from said pollinating by embryo rescue; and (e) obtaining an interspecific hybrid plant resulting from the growth of said embryo.

12. An interspecific hybrid Euphorbia plant or part thereof prepared by the process of claim 10.

13. A process of preparing an interspecific hybrid Euphorbia plant comprising the steps of:

a) obtaining a cutting of an interspecific hybrid Euphorbia plant produced from the cross of *Euphorbia pulcherrima* as a female parent and *Euphorbia cornastra* as a male parent; and b) cultivating said cutting to obtain an interspecific hybrid Euphorbia plant.

14. The process of claim 13, further defined as comprising applying a hormone composition to said cutting to induce formation of roots.

15. An interspecific hybrid Euphorbia plant prepared by the process of claim 13.

16. A process of altering the plant growth characteristics of an interspecific hybrid Euphorbia plants produced from a cross of *Euphorbia pulcherrima* and *Euphorbia cornastra*, the process comprising the steps of:
  (a) providing a plant having free-branching characteristics to be used as understock;
  (b) obtaining a scion of an interspecific hybrid Euphorbia plant produced from the cross of *Euphorbia pulcherrima* as a female parent and *Euphorbia cornastra* as a male parent;
  (c) making a graft union between the cellular tissue of the understock plant and the scion, whereby the characteristics of a vegetative shoot arising from said scion of said interspecific hybrid Euphorbia plant are altered; and
  (d) cultivating said shoot to obtain an interspecific hybrid Euphorbia plant comprising altered growth characteristics.

17. The process of claim 16, wherein said altered growth characteristics are further defined as comprising altered branching characteristics.

18. An interspecific hybrid Euphorbia plant prepared by the process of claim 16.

19. A plant part of the interspecific hybrid Euphorbia plant of claim 15.

20. The plant part of claim 19, further defined as a flower.

21. The plant part of claim 19, further defined as a cutting.

22. The plant part of claim 19, further defined as pollen.

23. The plant part of claim 19, further defined as an ovule.

24. The plant part of claim 19, further defined as a cell.

25. An interspecific hybrid Euphorbia plant or part thereof, clonally propagated from the plant of claim 18.

* * * * *

UNITED STATES PATENT AND TRADEMARK OFFICE
CERTIFICATE OF CORRECTION

PATENT NO. : 6,515,200 B1  
DATED : February 4, 2003  
INVENTOR(S) : Ruth Kobayashi It is certified that error appears in the above-identified patent and that said Letters Patent is hereby corrected as shown below:

<u>Title page,</u>  
Item [57], ABSTRACT,  
Line 6, please insert -- to -- between "found" and "have".  
Line 10, please insert -- , -- after "same".  
Line 11, please insert -- as -- between "well" and "methods".

<u>Column 12,</u>  
Line 30, please insert -- , -- after "thereof".

<u>Column 13,</u>  
Line 2, please delete "plants" and insert -- plant -- therefor.

Signed and Sealed this

Twenty-seventh Day of May, 2003

JAMES E. ROGAN  
*Director of the United States Patent and Trademark Office*